US005834184A

United States Patent [19]
Harada et al.

[11] Patent Number: 5,834,184
[45] Date of Patent: Nov. 10, 1998

[54] IN VIVO SELECTION OF RNA-BINDING PEPTIDES

[76] Inventors: Kazuo Harada, 611 Bobstay La., Foster City, Calif. 94404; Shelley S. Martin, 1261 Broderick St. #105, San Francisco, Calif. 94115; Alan Frankel, 50 Monte Cimas Ave., Mill Valley, Calif. 94941

[21] Appl. No.: 442,461

[22] Filed: May 17, 1995

[51] Int. Cl.⁶ .................................. C12Q 1/68; C12N 1/20
[52] U.S. Cl. ............................................. 435/6; 435/252.1
[58] Field of Search ....................................... 435/6, 252.1

[56] References Cited

U.S. PATENT DOCUMENTS 5,270,163 12/1993 Gold et al. .................................... 435/6
5,496,938 3/1996 Gold et al. .............................. 536/22.1
5,498,530 3/1996 Schatz et al. ........................... 435/69.1

FOREIGN PATENT DOCUMENTS

WO91/17271 11/1991 WIPO .

OTHER PUBLICATIONS

Burd et al., "Conserved structures and diversity of functions of RNA-binding proteins," *Science* 265, 615–621 (1994).
Chen et al., "An RNA-binding peptide from bovine immunodeficiency virus tat protein recognizes an unusual RNA structure," *Biochemistry* 33, 2708 (1994).
Franklin, "Clustered arginine residues of bacteriophage λ N protein are essential to antitermination of transcription, but their locale cannot compensate for boxB loop defects," *J. Mol. Biol.* 231, 343–360 (19930.
Karn et al., "New insights into the mechanism of HIV–1 trans–activation," *Trends Genet.* 8, 365 (1992).
Lazinski, "Sequence–specific recognition of RNA hairpins by bacteriophage antiterminators requires a conserved arginine–rich motif," *Cell* 59, 207–218 (1989).
MacWilliams et al., "Direct genetic selection for a specific RNA–protein interaction,"*Nucleic Acids. Res.* 21:24, 5754–5760 (1993).
Selby et al., "Trans–activation by HIV–1 Tat via a heterologous RNA binding protein," *Cell* 62, 769–776 (1990).
Stripeke et al., "Proteins binding to 5' untranslated regino sites: a general mechanism for translational regulation of mRNAs in human and yeast cells," *Mol Cell. Biol.* 14:9, 5898–5909 (1994).
Venkatesan et al., "Human immunodeficiency virus type 1 Rev activation can be achieved without Rev–responsive element RNA if Rev is directed to the target as a Rev/MS2 fusion protein which tethers the MS2 operator RNA," *J. Virol.* 66:12, 7469–7480 (1992).
Zapp et al., "Oligomerization and RNA binding domains of the type 1 human immunodeficiency virus Rev protein: a dual function for an arginine–rich binding motif," *Proc. Natl. Acad. Sci. USA* 88, 7734–7738 (1991).
Das, A. Journal of Bacteriology, 174(21):6711–6716. 1992.

*Primary Examiner*—Douglas W. Robinson
*Assistant Examiner*—Thanda Wai
*Attorney, Agent, or Firm*—Townsend & Townsend Crew

[57] ABSTRACT

The invention provides methods and kits suitable for large-scale in vivo screening of polypeptides for specific binding affinity to a selected RNA recognition sequence. Polypeptide (s) are screened as fusion proteins with a polypeptide having antitermination activity. Polypeptides having binding activity are identified by their capacity to activate transcription of a reporter gene via binding of the polypeptide being screened to the selected RNA recognition sequence. The invention also provides methods of screening RNA molecules for binding to a selected polypeptide.

23 Claims, 5 Drawing Sheets

FIG. 2

| N FUSION PROTEIN | | β-GAL EXPRESSION | |
|---|---|---|---|
| | | X-GAL | ONPG |
| M [REV 34-50] | | +++ | 139 |
| M [____] AAAAR | | ++++ | 175 |
| M [____] GGG | | ++ | 23 |
| MAAAA [____] AAAAGGG | | + | 15 |
| | | | |
| M [REV 34-47] | | +++ | 76 |
| M [____] GGG | | ++ | 5.9 |
| MAAAA [____] AAAAGGG | | + | 6.8 |
| MAAAA [____] AAAAN | | ++ | 14 |
| MAAAA [____] AAN | | ++ | 8.0 |
| MAAAA [____] N | | ++ | 6.1 |
| MA [____] AAAAN | | +++ | 141 |
| MA [____] AAAAN | | +++ | 90 |
| | | | |
| M [BIV TAT 65-81] | | +++ | 45 |
| | | | |
| M [BIV TAT 68-81] | | ++ | 33 |
| M [____] GGG | | +++ | 93 |
| MAAAA [____] AAAAGGG | | ++ | 44 |
| MG [____] GGGN | | +++ | 88 |

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

Thr Arg Gln Ala Arg Arg Asn Arg Arg Arg Arg Trp Arg Arg
    1                    5                                    10

( 2 ) INFORMATION FOR SEQ ID NO:2:

( i ) SEQUENCE CHARACTERISTICS:
        ( A ) LENGTH: 19 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:2:

CAGGGGATTT GCTGCATTC 19

(2) INFORMATION FOR SEQ ID NO:3:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:3:

Ser Arg Gln Ala Arg Arg Asn Arg Arg Arg Arg Trp Arg Arg
1               5                   10

(2) INFORMATION FOR SEQ ID NO:4:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:4:

Ser Arg Ser Ser Arg Arg Asn Arg Arg Arg Arg Arg Arg Arg
1               5                   10

(2) INFORMATION FOR SEQ ID NO:5:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:5:

Ser Arg Ser Arg Arg Arg Asn Arg Arg Arg Arg Arg Arg Arg
1               5                   10

(2) INFORMATION FOR SEQ ID NO:6:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:6:

Asn His Arg Arg Arg Arg Arg His Arg Arg Arg Arg Arg Arg
1               5                   10

(2) INFORMATION FOR SEQ ID NO:7:

(i) SEQUENCE CHARACTERISTICS:
(A) LENGTH: 14 amino acids
(B) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:7:

```
Asn His Arg Arg Arg Arg Arg Gln Arg Arg Arg Arg Arg
1               5                   10
```

( 2 ) INFORMATION FOR SEQ ID NO:8:

( i ) SEQUENCE CHARACTERISTICS:
( A ) LENGTH: 14 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:8:

```
Asn Ser Arg Arg Arg Arg Arg His Arg Arg Arg Arg Arg
1               5                   10
```

( 2 ) INFORMATION FOR SEQ ID NO:9:

( i ) SEQUENCE CHARACTERISTICS:
( A ) LENGTH: 14 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:9:

```
Asn Ser Arg Arg Arg Arg Arg Gln Arg Arg Arg Arg Arg
1               5                   10
```

( 2 ) INFORMATION FOR SEQ ID NO:10:

( i ) SEQUENCE CHARACTERISTICS:
( A ) LENGTH: 14 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:10:

```
Asn Arg Arg Arg Arg Arg Arg Gln Arg Arg Arg Arg Arg
1               5                   10
```

( 2 ) INFORMATION FOR SEQ ID NO:11:

( i ) SEQUENCE CHARACTERISTICS:
( A ) LENGTH: 14 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:11:

```
Asn His Arg Arg Arg Arg Arg Asn Arg Arg Arg Arg Arg
1               5                   10
```

( 2 ) INFORMATION FOR SEQ ID NO:12:

( i ) SEQUENCE CHARACTERISTICS:
( A ) LENGTH: 14 amino acids
( B ) TYPE: amino acid ( C ) STRANDEDNESS:
        ( D ) TOPOLOGY: linear ( i i ) MOLECULE TYPE: peptide ( x i ) SEQUENCE DESCRIPTION: SEQ ID NO:12:

Arg  His  Arg  Arg  Arg  Arg  Arg  Gln  Arg  Arg  Arg  Arg  Arg  Arg
    1                   5                        10

( 2 ) INFORMATION FOR SEQ ID NO:13:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

Ser  Arg  Xaa  Xaa  Arg  Arg  Asn  Xaa  Xaa  Xaa  Arg  Xaa  Xaa  Xaa
    1                   5                        10

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: RNA ( x i ) SEQUENCE DESCRIPTION: SEQ ID NO:14:

UCUGGGCGCA  GCGCAAGCUG  ACGGUACAGA                                                                  30

( 2 ) INFORMATION FOR SEQ ID NO:15:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:15:

Met  Asp  Ala  Gln  Thr  Arg  Arg  Arg  Glu  Arg  Arg  Ala  Glu  Lys  Gln  Ala
    1                   5                        10                       15

Gln  Trp  Asn ( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: RNA ( x i ) SEQUENCE DESCRIPTION: SEQ ID NO:16:

GGCCUGAAGA  AGGCC                                                                                   15

( 2 ) INFORMATION FOR SEQ ID NO:17:

( i ) SEQUENCE CHARACTERISTICS:
        ( A ) LENGTH: 14 amino acids
        ( B ) TYPE: amino acid (C) STRANDEDNESS:
        (D) TOPOLOGY: linear (ii) MOLECULE TYPE: peptide (xi) SEQUENCE DESCRIPTION: SEQ ID NO:17:

Arg Pro Arg Gly Thr Arg Gly Lys Gly Arg Arg Ile Arg Arg
1               5                   10

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: RNA (xi) SEQUENCE DESCRIPTION: SEQ ID NO:18:

UCGUGUAGCU CAUUAGCUCC GA                                                        22

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

Arg Lys Lys Arg Arg Gln Arg Arg Arg
1               5

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: both
        (D) TOPOLOGY: linear (ii) MOLECULE TYPE: RNA (xi) SEQUENCE DESCRIPTION: SEQ ID NO:20:

AGAUCUGAGC CUGGGAGCUC UCU                                                       23

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Gly Gly Gly Ser Gly Gly Gly Ser Gly Gly Gly Ser Gly Gly Gly Ser
1               5                   10                  15

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:22:

NNKNNKNNKN NKNNK                                                                                        15

( 2 ) INFORMATION FOR SEQ ID NO:23:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:23:

NNKNNKNNKN NKNNKNNK                                                                                     18

( 2 ) INFORMATION FOR SEQ ID NO:24:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:24:

NNKNNKNNKN NKNNKNNKNN K                                                                                 21

( 2 ) INFORMATION FOR SEQ ID NO:25:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:25:

NNKNNKNNKN NKNNKNNKNN KNNK                                                                              24

( 2 ) INFORMATION FOR SEQ ID NO:26:

( i ) SEQUENCE CHARACTERISTICS:
  ( A ) LENGTH: 21 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:26:

Met Ala Thr Arg Gln Ala Arg Arg Asn Arg Arg Arg Arg Trp Arg Arg
1               5                   10                  15
Ala Ala Ala Ala Asn
            20

( 2 ) INFORMATION FOR SEQ ID NO:27:

( i ) SEQUENCE CHARACTERISTICS:
  ( A ) LENGTH: 20 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:27:

Met Gly Arg Pro Arg Gly Thr Arg Gly Lys Gly Arg Arg Ile Arg Arg
1               5                   10                  15
Gly Gly Gly Asn
            20

( 2 ) INFORMATION FOR SEQ ID NO:28:

( i ) SEQUENCE CHARACTERISTICS:
 ( A ) LENGTH: 10 amino acids
 ( B ) TYPE: amino acid
 ( C ) STRANDEDNESS:
 ( D ) TOPOLOGY: linear ( i i ) MOLECULE TYPE: peptide ( x i ) SEQUENCE DESCRIPTION: SEQ ID NO:28:

Met Arg Lys Lys Arg Arg Gln Arg Arg Arg
1               5                   10

( 2 ) INFORMATION FOR SEQ ID NO:29:

( i ) SEQUENCE CHARACTERISTICS:
 ( A ) LENGTH: 4 amino acids
 ( B ) TYPE: amino acid
 ( C ) STRANDEDNESS:
 ( D ) TOPOLOGY: linear ( i i ) MOLECULE TYPE: peptide ( x i ) SEQUENCE DESCRIPTION: SEQ ID NO:29:

Arg Ser Asn His
1

( 2 ) INFORMATION FOR SEQ ID NO:30:

( i ) SEQUENCE CHARACTERISTICS:
 ( A ) LENGTH: 90 base pairs
 ( B ) TYPE: nucleic acid
 ( C ) STRANDEDNESS: single
 ( D ) TOPOLOGY: linear ( i i ) MOLECULE TYPE: DNA ( x i ) SEQUENCE DESCRIPTION: SEQ ID NO:30:

```
AGGAGAATCC CCATGGCCMR TMRTMRTMRT MRTMRTMRTM RTMRTMRTMR TMRTMRTMRT        60
GCAGCTGCGG CGAATGCAGC AAATCCCTG                                         90
```

( 2 ) INFORMATION FOR SEQ ID NO:31:

( i ) SEQUENCE CHARACTERISTICS:
 ( A ) LENGTH: 5 amino acids
 ( B ) TYPE: amino acid
 ( C ) STRANDEDNESS:
 ( D ) TOPOLOGY: linear ( i i ) MOLECULE TYPE: peptide ( x i ) SEQUENCE DESCRIPTION: SEQ ID NO:31:

Ala Ala Ala Ala Arg
1               5

( 2 ) INFORMATION FOR SEQ ID NO:32:

( i ) SEQUENCE CHARACTERISTICS:
 ( A ) LENGTH: 5 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:32:

Met Ala Ala Ala Ala
1               5

(2) INFORMATION FOR SEQ ID NO:33:

(i) SEQUENCE CHARACTERISTICS:
    (A) LENGTH: 7 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:33:

Ala Ala Ala Ala Gly Gly Gly
1               5

(2) INFORMATION FOR SEQ ID NO:34:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:34:

Ala Ala Ala Ala Asn
1               5

(2) INFORMATION FOR SEQ ID NO:35:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:35:

Gly Gly Gly Asn
1

IN VIVO SELECTION OF RNA-BINDING PEPTIDES

GOVERNMENT INTEREST

This invention was made with Government support under Grant No. GM47478, awarded by the National Institutes of Health. The Government has certain rights in this invention.

TECHNICAL FIELD

The invention applies the technical fields of combinatorial chemistry and molecular genetics to the isolation of RNA binding polypeptides. The RNA binding polypeptides are used in, e.g., therapy and diagnosis of pathogenic microorganisms.

BACKGROUND

RNA-binding proteins are known to fulfill a large number of diverse roles in different organisms. See generally Burd & Dreyfuss, *Science* 265, 615–621 (1994). In RNA viruses, such as HIV, RNA-binding proteins play essential roles in expression of viral genes. For example, HIV encodes two RNA binding proteins, termed Tat and Rev. Rev is a regulatory RNA binding protein that facilitates the export of unspliced HIV pre mRNA from the nucleus. Malim et al., *Nature* 338, 254 (1989). Tat is thought to be a transcriptional activator that functions by binding a recognition sequence in 5' flanking mRNA. Karn & Graeble, *Trends Genet.* 8, 365 (1992). Therapeutic compositions for inhibiting the interactions of Rev with its target are discussed by commonly owned co-pending U.S. application Ser. No. 08/071,811 (incorporated by reference in its entirety for all purposes). In bacteria, RNA binding proteins are known, inter alia, to have a role in activation of genes encoding ribosomal proteins. Li et al., *Cell* 38, 851–860 (1984). In mammalian cells, mutations in RNA binding proteins have been correlated with several defects or diseases. For example defects in genes encoding RNA binding proteins have been reported to result in azoospermia (Baker, *Nature* 340, 521 (1989)) and fragile X mental retardation syndrome (Siomi et al., *Science* 282, 563 (1993)). Mutations in several RNA binding proteins have been reported to cause developmental defects in Drosophila. Robinow et al., *Science* 242, 1570 (1988).

In recent years, there have been several developments in methods of isolating polypeptides having a desired binding specificity. These methods include the phage display technique in which polypeptides are displayed as a coat protein from a bacteriophage and screened against an immobilized receptor. See, e.g., Dower et al., WO 91/17271; McCafferty et al., WO 92/01047.; Ladner, U.S. Pat. No. 5,223,409 (incorporated by reference in their entirety for all purposes). The method permits mass screening of large libraries of polypeptides. However, applications of the method have largely been confined to screening protein-protein binding. Other mass screening methods have been developed for isolating nucleic acid sequences that bind to proteins. See Gold et al., U.S. Pat. No. 5,270,163. Both the phage-display method and Gold's method screen binding in vitro. Ladner et al., U.S. Pat. No. 5,096,815 and U.S. Pat. No. 5,198,346 have proposed in vivo methods for screening DNA binding proteins.

There have also been a number of studies investigating the structure and function of RNA binding proteins. Selby & Peterlin, *Cell* 62, 769–776 (1990) and Venkatesan et al., *J. Virol.* 66, 7469–7480 (1992) have reported that a eucaryotic transcriptional activator is functional when bound to RNA via a foreign peptide. Stripeke et al., *Mol. Cell. Biol.* 14, 5898–5908 (1994) have reported that insertion of a binding site for a phage coat protein 5' to a eucaryotic mRNA results in suppression of translation in the presence of the coat protein. Franklin, *J. Mol. Biol.* 231, 343–360 (1993) has discussed methods of screening for variants of the phage λ N antiterminator protein, and reported an arginine rich domain at the N-terminus of the protein in which mutations impair antiterminator function. MacWilliams et al., *Nucleic Acids. Res.* 21, 5754–5760 (1993) have discussed a modified P22 phage in which the ribosome binding site of the ant gene (responsible for the lytic state) was replaced with the RNA binding site of a different phage R17 protein. Mutants of the RNA binding site were screened by propagating the hybrid phage in cells expressing an R17 translational inhibitor with affinity for the ribosome binding site and determining the relative numbers of lysogenic to lytic phage.

Notwithstanding these developments, there remains a need for efficient methods of large-scale screening of RNA binding proteins in vivo. The present invention fulfills this and other needs.

SUMMARY OF THE INVENTION

The invention provides methods and kits for screening one or more polypeptides for specific binding affinity for a selected RNA recognition sequence. Some methods screen a plurality of polypeptides with potential RNA binding activity for binding to a selected RNA recognition sequence. In these methods, a library of cells is cultured. Each cell in the library comprises first and second DNA segments, which may be present on the same or different vectors. The first DNA segment supplies the polypeptides to be tested. The first DNA segment thus encodes a fusion protein comprising a fragment of an anti-terminator protein having anti-terminator activity linked in-frame to a polypeptide under test which varies between cells in the library. The second DNA segment supplies the reporter system. The second DNA segment encodes, in operable linkage, a promoter, an RNA recognition sequence foreign to the anti-terminator protein, a transcription termination site and a reporter gene. The termination site blocks transcription of the reporter gene in the absence of a protein with anti-termination activity and affinity for the RNA recognition sequence. The first DNA segment is expressed to yield the fusion protein, which, if the polypeptide under test has a specific affinity for the recognition sequence, binds via the polypeptide to the RNA recognition sequence of a transcript from the second DNA segment thereby inducing transcription of the second DNA segment to proceed through the termination site to the reporter gene resulting in expression of the reporter gene. Expression of the reporter gene is detected in a cell from the library. The expression indicates that the cell comprises a polypeptide having RNA binding activity.

Often the library of cells are procaryotic cells, preferably *E. coli*. Often the antiterminator protein is a phage antiterminator protein, such as the phage λ N protein. In such case, the second DNA segment usually also encodes a Box A sequence. The Box A sequence interacts with a host elongation factor stimulating antitermination activity of the fusion protein.

In some methods the polypeptides being screened are random polypeptides. In some methods, the polypeptides are variants of naturally occurring polypeptide such as the HIV Rev protein. In other methods, the polypeptides are naturally occurring polypeptides from a cDNA or genomic library. The number of polypeptides to be screened can be quite large (e. g., about $10^8$).

The invention further provides methods for screening a library of RNA fragments for binding activity to a selected polypeptide. These methods are analogous to the methods of screening polypeptides, except that the polypeptide is kept constant and the RNA molecules are varied. In these methods, a library of cells is cultured. Each cell comprises first and second DNA segments, which may be present on the same or separate vectors. The first DNA segment encodes a fusion protein comprising a fragment of a procaryotic anti-terminator protein having anti-terminator activity linked in-frame to a selected polypeptide. The second DNA segment encodes, in operable linkage, a promoter, an RNA sequence varying between different cells in the library, a termination site and a reporter gene, wherein the termination site blocks transcription of the reporter gene unless the RNA sequence has a specific affinity for the selected polypeptide. The first DNA segment is expressed to yield the fusion protein, which, if the RNA sequence has a specific affinity for the selected polypeptide, binds via the selected polypeptide to the RNA sequence of a transcript from the second DNA segment thereby inducing transcription of the second DNA segment to proceed through the termination site to the reporter gene resulting in expression of the reporter gene. Expression of the reporter gene in a cell from the library is detected indicating that the cell comprises an RNA sequence having affinity for the polypeptide. The cell may then be isolated.

In another aspect the invention provides kits for screening polypeptides for binding to an RNA molecule (or vice versa). The kits comprise recombinant DNA segments incorporated in one or more vectors, as described above.

BRIEF DESCRIPTION OF THE FIGURES

FIG. 2: Effect of amino acid context and peptide length on HIV Rev and BIV Tat peptide activities. Amino acids 1–19 of the $\lambda$ N protein were replaced with the peptides shown (SEQ ID NOS: 31–35). The $Rev_{34-47}$ peptides contain a substitution of glutamic acid 47 to arginine, included to maintain the overall charge of the peptide. Antitermination assays were performed with corresponding RRE and BIV TAR reporters.

DEFINITIONS

Figure 1:
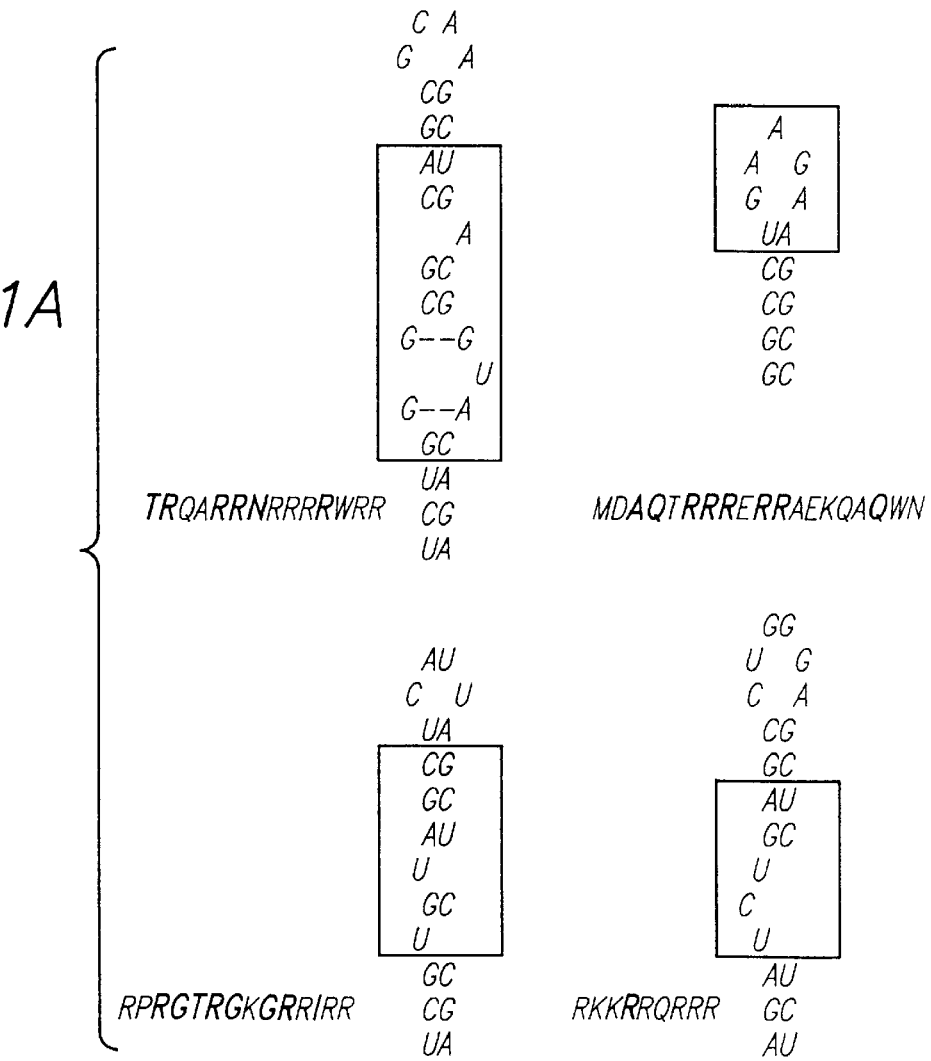
Fig. 1A: Arginine-rich peptides and their specific RNA-binding sites: HIV $Rev_{34-47}$ (SEQ ID NO:1) (glutamic acid at position 47 substitution with arginine) and RRE IIB (SEQ ID NO: 14) (top left); $\lambda$ $N_{1-9}$ (SEQ ID NO: 15) and Box B (top right) (SEQ ID NO: 16); BIV $Tat_{68-81}$ (SEQ ID NO: 17) and BIV TAR (SEQ ID NO: 18) (bottom left); HIV $Tat_{49-57}$ (SEQ ID NO: 19) and HIV TAR (SEQ ID NO: 20) (bottom right). Amino acids important for binding are indicated in bold and binding sites in the RNAs are boxed. Important amino acids in $\lambda$ N are tentatively assigned from mutagenesis of the intact protein (Franklin, supra).
FIG. 1B: The genetic code viewed from the perspective of arginine-rich peptides. Amino acids important for binding in the four peptide model systems are indicated in bold. A restricted genetic code (bold box) encodes all charged and hydrophilic residues, glycine, and proline, and contains all six arginine codons.

A specific binding affinity of an RNA binding polypeptide for an RNA binding site refers to a dissociation constant $\leq 10$ μM, preferably $\leq 100$ nM and most preferably $\leq 10$ nM, and the capacity to bind one (or more) RNA binding sites more strongly (i.e., at least 5-fold, 10-fold, 100-fold or 1000-fold) than others. Dissociation constants as low as 1 nM, 1 pM or 1 fM are possible for protein-RNA binding.

A DNA segment is operably linked when placed into a functional relationship with another DNA segment. For example, a promoter is operably linked to a coding sequence if it stimulates the transcription of the sequence. Generally, DNA sequences that are operably linked are contiguous, and in the case of two amino acid coding sequences, both contiguous and in reading phase. Linking is accomplished by ligation at convenient restriction sites or at adapters or linkers inserted in lieu thereof.

Peptide or polypeptide refers to a polymer in which the monomers typically are alpha-(L)-amino acids joined together through amide bonds. Peptides are at least two and usually three or more amino acid monomers long. Standard abbreviations for amino acids are used (see Stryer, *Biochemistry* (3rd ed., 1988) incorporated by reference in its entirety for all purpsoses). The term protein is used to refer to a full-length natural polypeptide or a synthetic polypeptide that is sufficiently long to have a self-sustaining secondary structure (e.g., α-helix or β-pleated sheet) and at least one functional domain.

Random peptide refers to an oligomer composed of two or more amino acid monomers and constructed by a means with which one does not entirely preselect the complete sequence of a particular oligomer.

A random peptide library refers not only to a set of recombinant DNA vectors (also called recombinants) that encodes a set of random peptides, but also to the set of random peptides encoded by those vectors, as well as the set of fusion proteins containing those random peptides. Random peptide libraries frequently contain as many as $10^6$ to $10^{12}$ different compounds.

The lefthand direction of a polypeptide is the amino terminal direction and the righthand direction is the carboxy-terminal direction, in accordance with convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand which are 5' the RNA transcript are referred to as "upstream sequences"; sequence regions on the DNA strand which are 3' to the RNA transcript are referred to as "downstream sequences."

A variant of a natural polypeptide usually exhibits at least 20%, and more usually at least 50%, sequence similarity to the natural polypeptide. The term sequence similarity means peptides have identical or similar amino acids (i.e., conservative substitutions) at corresponding positions.

The polypeptides of the present invention are obtained in a substantially pure form, typically being at least 50% weight/weight (w/w) or higher purity, and being substantially free of interfering proteins and contaminants, such as those which may result from expression in cultured cells. Preferably, the peptides are purified to at least 80% w/w purity, more preferably to at least 95% w/w purity. For use in pharmaceutical compositions, the polypeptide purity should be very high, typically being at least 99% w/w purity, and preferably being higher.

DETAILED DISCLOSURE

I. General

The invention provides methods of screening for RNA binding proteins that have desirable binding characteristics to selected RNA sequences. The methods can be used to isolate variants of known RNA binding proteins having altered (usually strengthened) binding characteristics. The methods are also useful for isolating hitherto unknown RNA binding proteins to any RNA sequence of interest. The unknown RNA binding proteins may be natural proteins encoded by cDNA or genomic libraries or synthetic peptides selected from a random combinatorial library. The methods can also be applied to screening a library of RNA recognition sequences to an RNA binding protein of interest.

II. The Screening System

The screening system has two recombinant DNA components. A first DNA segment encodes the polypeptide to be screened for RNA binding activity, and the second segment encodes a reporter system to detect the presence of such activity. In the first DNA segment the polypeptide to be screened is fused in-frame to a fragment of an antiterminator protein such that the combined coding sequence is operably linked to a promoter. The promoter should be compatible with the cell type in which screening is to be performed. Suitable promoters for use in the preferred cell-type, E. coli, include tac, trp, lac, T3 or T7. Antiterminator proteins include the N proteins of phages λ, 21 and P22, which have been completely sequenced. See Franklin, J. Mol. Biol. 181, 85–91 (1985); Lazinski et al., Cell 59, 207–218 (1989).

The anti-terminator proteins of phages λ, 21 and P22 contain an arginine-rich domain corresponding to about amino acids 1–19 at the N-terminus of the protein. This domain is responsible for RNA binding activity of these antiterminator proteins, while the remainder of each protein confers anti-terminator activity. In the present invention, the RNA binding domain of the anti-terminator protein is usually deleted and replaced with the polypeptide to be screened. Thus, the polypeptide being screened is fused to a fragment of an antiterminator protein that retains antiterminator activity but usually lacks endogenous RNA binding activity.

It is not necessary that the fragment of the antiterminator protein be the minimum domain responsible for antiterminator activity. Although the natural RNA binding domain of the antiterminator protein is usually completely or partly deleted, such is probably not essential. Thus, for example, the sequence encoding the RNA binding protein to be screened may also be arranged in tandem with the endogenous RNA binding domain of the antiterminator protein. The fusion polypeptide usually comprises from N-terminus to C-terminus, the polypeptide being screened followed by the antiterminator domain. However, the components may also be assembled in other operable combinations.

In some arrangements, the polypeptide being screened is also fused to a linker or spacer polypeptide. The linker can be inserted between the polypeptide being screened and the antiterminator protein or on the side of the polypeptide distal to the antiterminator protein. A linker (or spacer) refers to a molecule or group of molecules that connects two molecules or two parts of a single molecule. A linker serves to place the two molecules in a preferred configuration, e.g., so that each domain is functional without steric hindrance from the other. The spacer can be as short as one residue or as many as five to ten to up to about 100 residues. The spacer residues may be somewhat flexible, comprising polyglycine, or $(Gly_3Ser)_4$ (SEQ ID NO: 21) for example. Alternatively, rigid spacers can be formed predominantly from Pro and Gly residues. Hydrophilic spacers, made up of charged and/or uncharged hydrophilic amino acids (e.g., Thr, His, Asn, Gln, Arg, Glu, Asp, Met, Lys, etc.), or hydrophobic spacers made up of hydrophobic amino acids (e.g., Phe, Leu, Ile, Gly, Val, Ala) can be used to present the RNA binding site with a variety of local environments.

In all of these arrangements, the first recombinant DNA segment expresses a fusion protein in which one component is the polypeptide to be tested for RNA binding activity and the second component has antiterminator activity.

The second recombinant DNA segment containing the reporter system has at least four components in operable linkage. The components are a promoter, an RNA binding site, a transcription termination site and a reporter gene. A box A site may also be present. Virtually any promoter functional in the cell type being screened can be used. Preferred promoters are the same as those listed above for the first DNA segment.

The reporter gene can be any gene that confers a selectable or screenable property when it is expressed. Suitable reporter genes include the β-galactosidase gene, antibiotic resistance genes, such as CAT or AMP, and genes having a fluorescent expression product such as the green fluorescent protein gene.

The choice of termination site for the second DNA segment is not usually critical. Termination sites are RNA sequences of 50–100 bases downstream from the translational stop site of a protein coding sequences. Frequently, RNA termination sites can fold to a hairpin structure. Termination sites are recognized by RNA polymerase as a signal to cease transcription. See Von Hippel, Science 255, 809 (1992). In eucaryotic cells, the selection of termination site depends on the promoter to which the reporter gene is linked. However, in procaryotic cells, an antitermination protein recognizes virtually any procaryotic termination site, so the choice of termination site is not critical. In some vectors, multiple termination sites are included in tandem.

A further component of the second DNA segment constituting the reporter system is a DNA sequence encoding a known or potential RNA binding sequence. The RNA binding site is usually foreign to the antitermination protein (or fragment thereof) encoded by the first DNA segment. That is, the RNA binding site is not naturally bound by the antitermination protein (or fragment thereof). In other words, if the antitermination protein is the phage λ N protein, an RNA binding site other than the Box B sequence in NutR or NutL is present. The Box B sequence of NutL or NutR may or may not be removed from the second DNA segment. Preferably, the Box B sequence is removed and replaced by the foreign RNA binding site. Usually, the foreign RNA binding bind lacks a specific affinity for the antitermination protein (or fragment thereof) encoded by the first DNA segment. The use of a foreign RNA binding site ensures that binding of the fusion protein to the RNA binding site occurs via the polypeptide moiety being screened rather than an endogenous RNA binding domain of the antiterminator protein. The possibility of binding through the endogenous RNA binding domain of the antiterminator protein can also be eliminated by deleting this domain.

Sometimes, (e.g., when the antiterminator protein is a phage protein) the second recombinant DNA segment includes a Box A site as an additional component. Box A is a conserved sequence originally defined as component of the Nut sequences present in phages λ, 21 and P22. Box A sequences also exist in a variety of antiterminated operons including the ribosomal RNA operons of $E.\ coli$. Friedman & Olson, *Cell* 34, 143–149 (1983); Li et al., *Cell* 38, 851–860 (1984). The complete sequences of Nut sites including Box A and Box B domains from phages λ, 21 and P22 are given by Lazinski, *Cell* 59, 207–218 (1989) (incorporated by reference in its entirety for all purposes). Box B is responsible for binding an antiterminator protein. Box A, a sequence of 8–12 nucleotides, which is proximal to the promoter in a natural operon, is responsible for binding a host elongation factor that interacts with the antitermination protein (or in the present methods the fusion protein having antitermination activity) to stimulate antitermination activity. See Greenblatt et al., *Nature* 364, 401–406 (1993) (incorporated by reference in its entirety for all purposes). The Box A domain should preferably match the antiterminator protein (or fragment thereof) encoded by the first segment. Thus, if the antiterminator protein is the phage λ N protein, one may choose aλ NutL or NutR Box A sequence, which differ slightly in nucleotide sequence. Analogously, if the termination protein is a phage P22 N protein, one may choose a P22 Nut Box A sequence.

The promoter and reporter gene are linked to achieve expression with the promoter upstream from the reporter. The RNA binding site and termination site are usually between the promoter and the reporter gene, with the RNA binding site proximal to the promoter. In some arrangements, Box A is present, usually between the promoter and the termination site. In a natural antitermination system, a Box A site is juxtaposed by a Box B site (e.g., in phage Nut sites). In the present reporter system, the Box B site may or may not be present. Preferably, Box B is absent and replaced by the foreign RNA binding site. The exact spacing of the components of the reporter system is not thought to be critical. All that is required is that the termination site blocks expression of the reporter gene from the promoter in the absence of a protein with antitermination activity and a specific binding affinity for the RNA recognition sequence.

Figure 5:
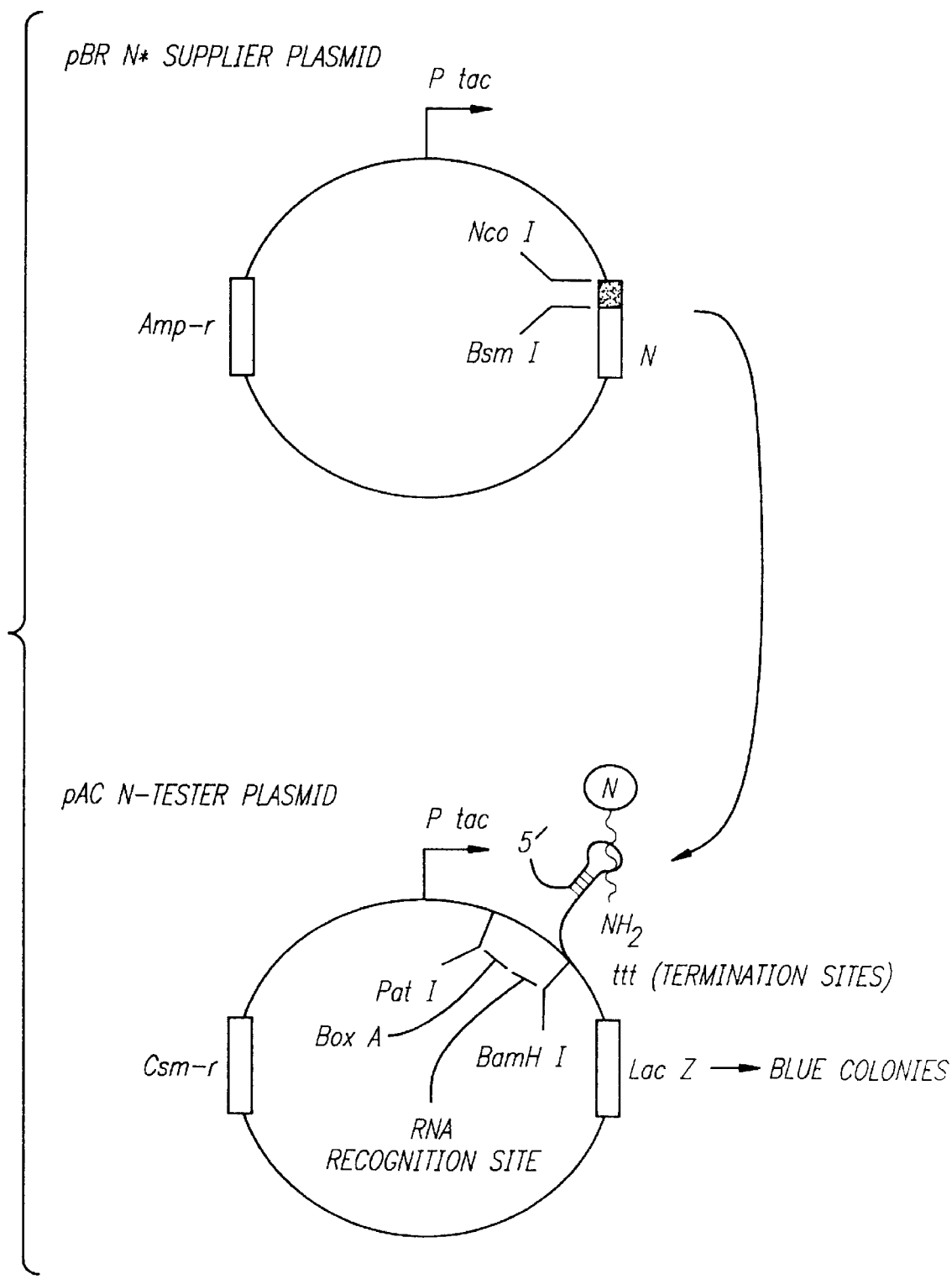
FIG. 5: Exemplary vectors for screening RNA binding polypeptides. Polypeptides are cloned between the NcoI and BsmI sites of pBRN* in-phase with a fragment of the phage $\lambda$ N protein. The plasmid expresses the polypeptide as a fusion protein from the tac promoter. The pACN-Tester plasmid encodes (clockwise) a promoter, a box A site, an RNA recognition site, three termination sites and a lacZ reporter gene. The fusion protein encoded by the pBRN* vector binds via the polypeptide moiety to the RNA recognition site thereby allowing transcription to proceed through the three termination sites to the lacZ reporter gene.

The two DNA segments can be contained in the same or separate DNA vectors. If separate vectors are used, the two vectors should have compatible origins of replication. Vectors can be introduced into cells by chemical transformation or electroporation. Electroporation is preferred for generation of large combinatorial libraries. Either a eucaryotic or procaryotic host cell line can be used. Any strain of bacteria (e.g., streptomyces, bacillus) compatible with the selected vectors is suitable. However, standard laboratory strains of $E.\ coli$ are preferred because of the higher transformation efficiencies obtainable. If two vectors are used, the vectors preferably contain different antibiotic resistance genes, allowing selection for cells maintaining both vectors. The antibiotic resistance genes used to ensure maintenance of plasmids should be different from any antibiotic resistance gene used as a reporter. Exemplary vectors are shown in FIG. 5.

After introduction of the two recombinant DNA segments into a cell, either on the same or separate vectors, the selection works as follows. The first DNA segment is expressed to yield a fusion protein. The fusion protein comprises a polypeptide to be screened for RNA binding activity and a second domain having antitermination activity. The second DNA segment is transcribed only to a limited extent. Transcription proceeds through the RNA binding site but is stopped by the termination site before it reaches the reporter gene. If the polypeptide being screened has a specific affinity for the RNA binding sequence included in the reporter system, the fusion protein binds to this sequence via the polypeptide being screened. The other portion of the fusion protein with antiterminator activity releases the blockage of transcription caused by the termination site. Thus, transcription proceeds through the reporter gene, which is expressed. If the polypeptide being screened lacks a specific affinity for the RNA recognition sequence, transcription of the reporter gene remains blocked. The presence of the reporter gene product therefore indicates that the polypeptide under test has RNA binding activity for the RNA binding sequence included in the reporter system.

III. RNA Binding Protein and Recognition Sequences

Natural RNA binding proteins often have one domain responsible for RNA binding and other domains responsible for other functions. The domain responsible for RNA binding can sometimes be recognized by a characteristic motif. The most widely found RNA recognition sequence or binding motif is the RNP motif. The RNP motif is a 90-100 amino acid sequence that is present in one or more copies in proteins that bind pre mRNA, mRNA, pre-ribosomal RNA and snRNA. The consensus sequence and the sequences of several exemplary proteins containing the RNP motif are provided by Burd and Dreyfuss, supra. See also Swanson et al., *Trends Biochem. Sci.* 13, 86 (1988); Bandziulis et al., *Genes Dev.* 3,431 (1989); Kenan et al., *Trends Biochem. Sci.* 16, 214 (1991). The consensus motif contains two short consensus sequences RNP-1 and RNP-2. Some RNP proteins bind specific RNA sequences with high affinities (dissociation constant in the range of $10^{-8}$–$10^{-11}$M). Such proteins often function in RNA processing reactions. Other RNP proteins have less stringent sequence requirements and bind less strongly (dissociation constant ~$10^{-6}$–$10^{-7}$M). Burd & Dreyfuss, *EMBO J.* 13, 1197 (1994).

A second characteristic RNA binding motif found in viral, phage and ribosomal proteins is an arginine-rich motif (ARM) of about 10–20 amino acids. RNA binding proteins having this motif include the HIV Tat and Rev proteins. Rev binds with high affinity disassociation constant ($10^{-9}$M) to an RNA sequence termed RRE, which is found in all HIV mRNAs. Zapp et al., *Nature* 342, 714 (1989); Dayton et al., *Science* 246, 1625 (1989). Tat binds to an RNA sequence termed TAR with a dissociation constant of $5\times10^{-9}$M. Churcher et al., *J. Mol. Biol.* 230, 90 (1993). For Tat and Rev proteins, a fragment containing the arginine-rich motif binds as strongly as the intact protein. In other RNA binding proteins with ARM motifs, residues outside the ARM also contribute to binding. Other families of RNA binding proteins with different binding motifs are described by Burd and Dreyfyss, supra.

IV. Combinatorial Strategies

In some embodiments, the methods of the invention are used to isolate RNA binding polypeptides to an RNA sequence known to bind a natural RNA binding protein. A selected RNA sequence is inserted into the second DNA segment (screening system) as described above and a library of polypeptides is inserted into the first DNA segment. The library of polypeptides can be a random library of short peptides about 6–25 amino acids long. The library can also constitute variant forms of a naturally occurring RNA binding protein. In this case, the naturally occurring RNA binding protein may or may not be the natural partner for the selected RNA binding site. The members of the library can be of similar length to a full-length naturally occurring RNA binding protein, or can be much shorter, including predominantly the RNA binding motif. If full-length proteins are to be screened, variant amino acids are concentrated in the RNA binding domain of the full-length protein. In some methods, all of the amino acids within an RNA binding domain are varied. In other methods, a framework of amino acids is kept constant, and only selected amino acids varied. The framework is usually formed from amino acids that contribute to the global three dimensional structure of the protein but do not directly contact the target RNA molecule. Selected residues for variation are preferably those that directly contact the target or amino acids proximal to such amino acids. In some polypeptides, at least five residues are selected for variation. The scope of variation at each position can encompass all twenty amino acids or a more limited repertoire. For example, for RNA binding proteins having an ARM motif, the repertoire might in some instances be limited to charged and hydrophilic residues.

In other methods, polypeptides to be screened are obtained from natural cDNA or genomic libraries. Such libraries are inserted into the first DNA segment as described above. These methods are particularly useful for isolating cognate and allelic variants of known RNA binding proteins.

The methods can also be used to identify RNA binding polypeptides to RNA sequences having no known binding protein. For example, one might want to isolate an RNA binding polypeptide to a unique RNA sequence that occurs in the RNA of a pathogen but does not occur in humans or other mammals. RNA sequences proximal to transcriptional or translation initiation sites are particular suitable. A DNA segment encoding the selected RNA sequence is cloned into the reporter system. A library of polypeptides, which can be random polypeptides or variants of a known RNA binding protein, is cloned into the first DNA segment and screened as described above.

The methods are also useful for isolating antibodies with a specific affinity for a selected RNA sequence. Libraries from unimmunized human B cells are prepared according to the general protocol outlined by Huse et al., *Science* 246:1275–1281 (1989). The heavy and light chains can be screened individually or as a complex for binding activity. For individual screening, a library of heavy (or light) chains is cloned into the first recombinant DNA segment in frame with the antiterminator protein. The library is then screened as for other libraries of potential RNA binding polypeptides. For screening a complex of both chains, the chains can be linked by a spacer and the combined heavy-spacer-light chain expressed as a fusion protein with the antiterminator protein. See Ladner, U.S. Pat. No. 5,260,203. Alternatively, one of the chains can be expressed as a fusion protein with the antiterminator protein or fragment (as for any other polypeptide being screened) and the other chain expressed from a separate promoter, which may be on the same or a different vector as the first chain.

In a further variation, the methods can be used to identify an RNA sequence that binds to a selected RNA binding protein. Such methods are useful, for example, in mapping the RNA binding site of the selected protein. In this situation, a DNA sequence encoding the selected protein (or the RNA binding domain thereof) is cloned into the first DNA segment (i.e., linked to the antiterminator domain) and a library of DNA encoding variable RNA segments is cloned into the second DNA segment (i.e., the reporter system). The library can be random, contain variants of a selected consensus sequence, or can contain a family of sequences varying in a systematic fashion. For example, to map an RNA binding site within the context of a larger RNA sequence, one requires a series of overlapping oligonucleotides encoding fragments of the RNA sequence.

Libraries are constructed by cloning an oligonucleotide which contains the variable region of library members (and any spacers and nonvariable framework determinants) into the selected cloning site. Using known recombinant DNA techniques (see generally, Sambrook et al., *Molecular Cloning, A Laboratory Manual*, 2d ed., Cold Spring Harbor Laboratory Press, Cold Spring Harbor, N.Y., 1989, incorporated by reference in its entirety for all purposes), an oligonucleotide may be constructed which, inter alia, removes unwanted restriction sites and adds desired ones, reconstructs the correct portions of any sequences which have been removed (such as a correct signal peptidase site, for example), inserts the spacer conserved or framework residues, if any, and corrects the translation frame (if necessary) to produce a fusion protein. A portion of the oligonucleotide will generally contain one or more variable region domain(s) and the spacer or framework residues. The sequences are ultimately expressed as peptides (with or without spacer or framework residues). The variable region domain of the oligonucleotide comprises the source of the library. The size of the library varies according to the number of variable codons, and hence the size of the peptides, which are desired. Generally the library will be at least about $10^4$ or $10^6$ members, usually at least $10^7$, and typically $10^8$ or more members.

To generate the collection of oligonucleotides which forms a series of codons encoding a random collection of amino acids and which is ultimately cloned into the vector, a codon motif is used, such as $(NNK)_x$, where N may be A, C, G, or T (nominally equimolar), K is G or T (nominally equimolar), and x is typically up to about 5 (SEQ ID NO: 22), 6 (SEQ ID NO: 23), 7 (SEQ ID NO: 24), or 8 (SEQ ID NO: 25) or more, thereby producing libraries of penta-, hexa-, hepta-, and octa-peprtides or more. The third position may also be G or C, designated "S". Thus, NNK or NNS (i) code for all the amino acids, (ii) code for only one stop codon, and (iii) reduce the range of codon bias from 6:1 to 3:1. The expression of peptides from randomly generated mixtures of oligonucleotides in appropriate recombinant vectors is discussed in Oliphant et al., *Gene* 44:177–183 (1986), incorporated herein by reference.

The codon motif $(NNK)_6$ (SEQ ID NO: 23) produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues. For example, a complete collection of hexacodons contains one sequence encoding each peptide made up of only one-codon amino acids, but contains 729 ($3^6$) sequences encoding each peptide with only three-codon amino acids.

An additional codon motif useful for generating diversity in RNA binding proteins having an ARM motif is CAG/CAG/N (see FIG. 1B). This limited genetic code allows synthesis of all charged and hydrophilic amino acids and is enriched in arginine residues. Combinations of these amino acids are expected to encode a variety of helical and non-helical arginine-rich RNA-binding peptides. Subsets of this restricted code may be devised to favor certain types of peptide structures and RNA interactions: boxed amino acids were used in the present peptide library experiment. Hydrophobic amino acids are excluded from the restricted code.

An alternative approach to minimize the bias against one-codon residues involves the synthesis of 20 activated tri-nucleotides, each representing the codon for one of the 20 genetically encoded amino acids. These are synthesized by conventional means, removed from the support but maintaining the base and 5-HO-protecting groups, and activating by the addition of 3'O-phosphoramidite (and phosphate protection with b-cyanoethyl groups) by the method used for the activation of mononucleosides, as generally described in McBride and Caruthers, *Tetrahedron Letters* 22:245 (1983), which is incorporated by reference herein. Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, *Oligonucleotide Synthesis*, M. J. Gait, ed. p35–82 (1984). Thus, this procedure generates a population of oligonucleotides for cloning that is capable of encoding an equal distribution (or a controlled unequal distribution) of the possible peptide sequences. This approach may be especially useful in generating longer peptide sequences, since the range of bias produced by the $(NNK)_6$ (SEQ ID NO: 23) motif increases by three-fold with each additional amino acid residue.

When the codon motif is $(NNK)_x$, as defined above(SEQ ID NO 22–25), and when x equals 8(SEQ ID NO: 25), there are $2.6 \times 10^{10}$ possible octa-peptides. A library containing most of the octa-peptides may be difficult to produce. Thus, a sampling of the octa-peptides may be accomplished by constructing a subset library using of about .1%, and up to as much as 1%, 5% or 10% of the possible sequences, which subset is then screened. As the library size increases, smaller percentages are acceptable. If desired, to extend the diversity of a subset library the recovered subset of sequences may be subjected to mutagenesis and then subjected to subsequent rounds of screening. This mutagenesis step may be accomplished in two general ways: the variable region of the recovered RNA binding polypeptides can be mutagenized, or additional variable amino acids may be added to the regions adjoining the initial variable sequences.

A variety of techniques can be used to diversify a peptide library or to diversify around peptides found in early rounds of screening to have substantial specific binding activity. In one approach, the positive RNA binding polypeptides are sequenced to determine the identity of the active peptides. Oligonucleotides are then synthesized based on these peptide sequences, employing a low level of all bases incorporated at each step to produce slight variations of the primary oligonucleotide sequences. This mixture of (slightly) degenerate oligonucleotides is then rescreened as described above. This method produces systematic, controlled variations of the starting peptide sequences.

Another technique for diversifying around the recognition kernel of a selected RNA binding polypeptide involves the subtle misincorporation of nucleotide changes in the peptide through the use of the polymerase chain reaction (PCR) under low fidelity conditions. Alteration of the ratios of nucleotides and the addition of manganese ions can produce a 2% mutation frequency. Yet another approach for diversifying the selected RNA binding polypeptides involves the mutagenesis of a pool, or subset, of recovered plasmids encoding polypeptides with binding activity. The plasmids are mutagenized by treatment with, e.g., nitrous acid, formic acid, or hydrazine. These treatments produce a variety of damage in the DNA. The damaged DNA is then copied with reverse transcriptase which misincorporates bases when it encounters a site of damage. The segment containing the sequence encoding the variable peptide is then isolated by cutting with restriction nuclease(s) specific for sites flanking the variable region. This mutagenized segment is then recloned and rescreened. See Myers et al., *Nucl. Acids Res.* 13:3131–3145 (1985), Myers et al., *Science* 229:242–246 (1985), and Myers, *Current Protocols in Molecular Biology Vol I*, 8.3.1–8.3.6 (Ausebel et al., eds., Wiley, N.Y. (1989)) (which are incorporated by reference in their entirety for all purposes).

In the second general approach, that of adding additional amino acids to a peptide or peptides found to be active, a variety of methods are available. In one, the sequences of peptides selected after a first screening are determined individually and new oligonucleotides, incorporating the determined sequence and an adjoining degenerate sequence, are synthesized. These are then cloned to produce a secondary library.

In another approach which adds a second variable region to a pool of plasmids encoding RNA binding polypeptides, a restriction site is installed next to the primary variable region. Preferably, the enzyme should cut outside of its recognition sequence, such as BspMI which cuts leaving a four base 5' overhang, four bases to the 3' side of the recognition site. Thus, the recognition site may be placed four bases from the primary degenerate region. To insert a second variable region, the pool of plasmid DNA is digested and blunt-ended by filling in the overhang with Klenow fragment. Double-stranded, blunt-ended, degenerately synthesized oligonucleotide is then ligated into this site to produce a second variable region juxtaposed to the primary variable region. This secondary library is then amplified and screened as before.

While in some instances it is appropriate to synthesize peptides having contiguous variable regions to bind certain RNA sequences, in other cases it is desirable to provide peptides having two or more regions of diversity separated by spacer residues. For example, the variable regions may be separated by spacers which allow the diversity domains of the peptides to be presented to the receptor in different ways. The distance between variable regions may be as little as one residue, sometimes five to ten and up to about 100 residues. For probing a large binding site the variable regions may be separated by a spacer of residues of 20 to 30 amino acids. The number of spacer residues when present will preferably be at least two, typically at least three or more, and often will be less than ten, more often less than eight residues.

Unless modified during or after synthesis by the translation machinery, recombinant peptide libraries consist of sequences of the 20 normal L-amino acids. While the available structural diversity for such a library is large, additional diversity can be introduced by a variety of means, such as chemical modifications of the amino acids. For example, a peptide library can have its carboxy terminal amidated. See Eipper et al., *J. Biol. Chem.* 266, 7827–7833 (1991).

V. Screening Procedures

After transformation of vector(s) into the host cells, the host cells are propagated in standard liquid or solid laboratory media to allow expression of the potential RNA binding polypeptides and the reporter plasmid. The method of screening depends on the reporter gene. If the reporter gene is β-galactosidase, cells are screened for expression of the reporter gene by plating on X-gal media. Cells expressing the gene give rise to blue colonies. The intensity of blue is positively correlated with the extent of expression of β-galactosidase, which is in turn positively correlated with the extent of binding of the potential RNA binding polypeptide contained within a colony. Thus, simple visual inspection of a plate gives some indication of the colonies containing the RNA binding polypeptides with strongest affinity. The extent of expression can be quantified more accurately by propagating liquid cultures from individual colonies on a plate and performing an ONPG assay on permeabilized cells (see Example 4).

In an analogous approach, when the reporter gene is a selectable gene such as CAT, colonies are plated on a selective media, and only colonies containing a polypeptide with specific affinity for the selected RNA recognition sequence grow. Colony size provides a simple visual indication of the affinity of the RNA binding protein. Affinity can be quantified more accurately by measuring CAT levels in liquid culture. Use of a selectable reporter gene is advantageous in that colonies can be plated at higher density allowing screening of larger libraries.

In a further approach, colonies are screened by FACS analysis. A fluorescent signal can be generated by treating cells containing a β-galactosidase reporter gene with the substrate fluorescein di-β-D-glactopyranoside, which breaks down to fluorescein. See Alvarex et al., *Biotechniques* 15, 975 (1993). Alternatively, the reporter gene can encode a fluorescent protein. The FACS method can screen large numbers of cells in liquid culture. A FACS machine can be programmed to isolate a fractionate of cells whose fluorescence exceeds a desired limit. These cells are those containing the polypeptides with the highest binding affinities.

In all screening methods, plasmids encoding polypeptides showing binding activity on a first screen can be pooled, if desired, retransformed into host cells and rescreened by the same general approach. The variable portion of plasmids are then sequenced to determine the nucleic acid sequence (and the deduced amino acid sequence) of the RNA binding proteins identified by the screening. RNA binding proteins can then be produced by, for example, synthesizing synthetic olignucleotides encoding the RNA binding protein and expressing the same in cell culture.

VI. Applications

RNA binding polypeptides isolated by the methods described above have a variety of uses. In one application, RNA binding polypeptides are used in therapeutic methods to block the life-cycle of pathogenic microorganisms, including viruses, such as HIV, and bacteria. Some synthetic RNA binding polypeptides are used as antagonists of a naturally occurring RNA binding protein. A synthetic polypeptide occupies the target site in competition with the natural protein without fulfilling the physiological role of the natural protein. The synthetic polypetpide thereby antagonizes the natural protein and aborts the life-cycle of a pathogenic microorganism. In such methods, the synthetic RNA binding polypeptide preferably has a higher binding affinity than the natural protein, and lacks functional domains (other than the binding domain) present in the natural protein. Other RNA binding polypeptides bind unique sequences on the pathogen's mRNA for which there may be no naturally occurring RNA binding protein. These polypeptide interfere with replication or translation of the pathogenic microorganism. For example, the RNA binding protein can occlude the Shine-Delgarno sequence or initiation codon of a bacterial mRNA thereby preventing translation. In mammalian diseases resulting from impairment or loss of a natural RNA binding protein, treatment with an exogenous RNA binding protein or an analog that substitutes for, or agonizes a natural protein serves to ameliorate the disease. Some of these synthetic polypeptides possess both an RNA binding protein and a functional domain also present in the naturally occurring protein.

The RNA binding proteins isolated by the methods also serve as lead compounds for the development of derivative compounds. The derivative compounds can include chemical modifications of amino acids or replace amino acids with chemical structures. The analogs should have a stabilized electronic configuration and molecular conformation that allows key functional groups to be presented to the RNA binding site in substantially the same way as the lead peptide. In particular, the non-peptidic compounds will have spatial electronic properties which are comparable to the polypeptide binding region, but will typically be much smaller molecules than the polypeptides, frequently having a molecular weight below about 2 kD and preferably below about 1 kD.

Identification of such non-peptidic compounds can be performed through use of techniques known to those working in the area of drug design. Such techniques include, but are not limited to, self-consistent field (SCF) analysis, configuration interaction (CI) analysis, and normal mode dynamics analysis. Computer programs for implementing these techniques are readily available. See Rein et al., *Computer-Assisted Modeling of Receptor-Ligand Interactions* (Alan Liss, N.Y., 1989).

RNA binding proteins or analogs are formulated for therapeutic use as pharmaceutical compositions. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The RNA binding polypeptide isolated by the methods are also useful in diagnostic methods. For example, an RNA binding polypeptide with a specific affinity for an RNA sequence encoded by a pathogenic microorganism can be used to detect the microorganism. In one assay format, the polypeptide is immobilized to a support, optionally via a linker, and a sample, which may or may not contain RNA from the microorganism, is contacted with the support. Bindings of the RNA from the microorganism to the support can be detected by competition with binding of a labelled synthetic RNA recognition sequence to the immobilized RNA binding polypeptide. RNA binding polypeptides are also useful in controlling the growth of cells in culture.

VII. Kits

The invention also provides kits useful for the screening methods. The kits contain the first and second DNA segments described in section II above, cloned into the same or separate vectors. The kits may also contain chemicals for performing a screen, such as X-gal, and primers suitable for sequencing the vectors. The kits usually include labelling or instructions indicating the suitability of the kits for screening DNA binding proteins and indicating how the vector(s) are to be used for that purpose. The term "label" is used generically to encompass any written or recorded material that is attached to, or otherwise accompanies the diagnostic at any time during its manufacture, transport, sale or use.

The following examples are provided to illustrate but not to limit the invention.

EXAMPLES

Example 1

Hybrid antiterminator protein

In this example, a pBR322-derived vector was constructed encoding a hybrid protein in which the 19-amino acid N-terminal RNA-binding sequence of the phage λ N protein was replaced by an arginine-rich putative RNA binding polypeptide from one of the following eucaryotic proteins, HIV RRE, BIV TAR, or HIV TAR.

Synthetic oligonucleotide cassettes encoding HIV Rev (maTRQARRNRRRRWRR-aaaan) (SEQ ID NO: 26), BIV Tat (mgRPRGTRGKGRRIRRgggn) (SEQ ID NO: 27), and HIV Tat (MRKKRRQRRR) (SEQ ID NO: 28) peptides were cloned into the unique BsmI and NcoI sites of pBRptacN* (Franklin, *J. Mol Biol* 231, 343 (1993)), creating fusion proteins at amino acid 20 of the λ N protein. The sequence encoding the fusion protein was linked to a tac promoter.

A second pACYC-derived vector was constructed encoding a tac promoter linked to the phage λ termination site Nut and a β-galactosidase structural gene. See Franklin, *J. Mol Biol* 231, 343 (1993). oligonucleotides containing box A of the Nut site and the appropriate RNA hairpin (FIG. 1A) in place of Box B were cloned into the unique PstI and BamHI sites of pACnutTAT13 (Id.), replacing the existing λ Nut site. Two additional GC base pairs were added at the ends of each hairpin stem.

Plasmids were transformed into *E. coli* strain N567 (Franklin & Doelling, *J. Bacteriol.* 171, 2513 (1989)) and bacteria were grown on LB plates or in tryptone broth containing 50 mg/l ampicillin and/or 15 mg/l chloramphenicol. In the β-galactosidase colony color assay, the number of +s represents visual estimation of blue intensity after growing colonies on plates containing 0.08 mg/ml X-gal and 0.024 mg/ml IPTG (to induce the tac promoters) for ~48 hr at 34° C. β-galactosidase activity was also measured in permeabilized cells using an ONPG colorimetric assay (Sambrook et al. *Molecular Cloning* (Cold Spring Harbor Laboratory Press, Cold Spring Harbor, 1989)). Bacteria were grown at 34° C. to early log phase, IPTG was added to 0.5 mM, and cells were grown for 1 additional hr to $OD_{600}$=0.4–0.5. The activity measured on plates and in permeabilized cells correlates roughly as follows: +++++, 200 units β-galactosidase/1 $OD_{600}$ unit cells; ++++, 100–200 units; +++, 10–100 units; ++, 2–10 units; +, 1–10 units; –, background.

Antitermination was observed only with specific peptide-RNA interactions (Table 1). The activities of HIV Rev and BIV Tat-N fusion proteins on their respective reporters were lower than wild-type N on the Nut reporter but were well above background levels. The plate assay appears to be particularly sensitive (see below). The lack of activity of the HIV Tat-N fusion protein on the HIV TAR reporter is likely because additional cellular factors are needed for high affinity binding. Jones & Peterlin, *Annu. Rev. Biochem.* 63, 717 (1994). Western analysis using anti-N polyclonal antiserum indicated that steady-state expression levels of each N fusion protein were slightly below that of wild-type N.

TABLE 1

Antitermination by N proteins fused to heterologous arginine-rich peptides

| Reporter | N-Fusion | X-gal | ONPG |
|---|---|---|---|
| Nut⁻ | N | – | 1.9 |
|  | Rev | – | 1.1 |
|  | BIV Tat | – | 0.6 |
|  | HIV Tat | – | 0.7 |
| Nut | N | +++++ | 1020 |
|  | Rev | – | 1.0 |
|  | BIV Tat | – | 1.1 |
|  | HIV Tat | – | 0.7 |
| HIV RRE | N | – | 2.5 |
|  | Rev | +++ | 17 |
|  | BIV Tat | – | 0.4 |
|  | HIV Tat | – | 0.6 |
| BIV TAR | N | – | 2.9 |
|  | Rev | – | 1.7 |
|  | BIV Tat | +++ | 21 |
|  | HIV Tat | – | 0.8 |
| HIV TAR | N | – | 2.4 |
|  | Rev | – | 1.5 |
|  | BIV Tat | – | 0.6 |
|  | HIV Tat | – | 0.9 |

Nut and Nut⁻(a Nut site deletion) reporters and the N-expressing plasmid are described in Franklin, J. Mol Biol 231, 343 (1993).

In summary, this example shows that a hybrid antiterminator protein containing a phage λ N protein antiterminator domain linked to a foreign RNA binding polypeptide is functional when bound to RNA via the foreign polypeptide. The hybrid protein exhibits antitermination activity on a termination site proximal to the RNA recognition sequence bound by the foreign polypeptide resulting in expressing of the reporter gene.

Example 2

Use of linkers to enhance display of RNA binding polypeptides

This example determines the most favorable local context in which to display a helical or nonhelical peptide. HIV Rev and BIV Tat peptides were fused into the λ N protein as described above (i.e., with the inserted peptide replacing amino acids 1–19 of the N protein) except that the N-protein and peptide domains were separated by a linker of four alanines or three glycines. The alanine linker increased activity of the Rev-N fusion protein whereas the glycine linker decreased activity (FIG. 2). The increase may be due to increase helicity imparted by the linker. Both HIV Rev and λ N proteins require α-helical conformations to bind specifically to their RNA sites. See Tan et al., *Cell* 73, 1031 (1993); Oubridge et al., *Nature* 372, 432 (1994). However, addition of a second alanine linker to the N-terminus of the fusion protein reduced activity, suggesting that factors other than peptide helicity can influence antitermination activity. For display of the BIV Tat peptide, a glycine linker between the peptide and the N-protein provided the most favorable context for display (FIG. 2). Additional experiments indicated that Rev and BIV Tat peptides could be shortened to 14 amino acids, from previously used 17-amino acid versions, with little effect on activity (FIG. 2). Thus, peptide library experiments described below were performed with 14 randomized positions and either alanine or glycine linkers.

Example 3
Random Mutagenesis of a single position in an RNA binding protein

Figure 3:
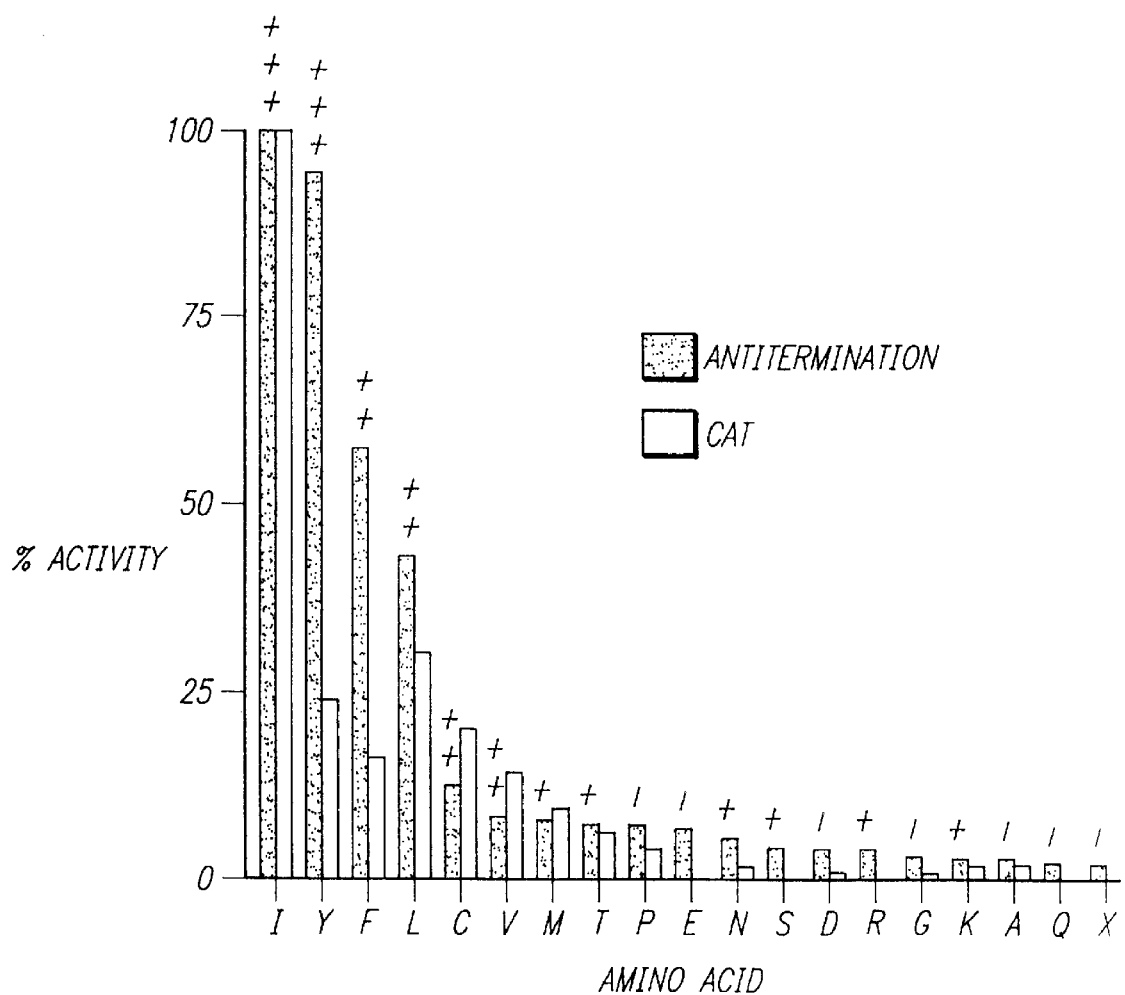
FIG. 3: Antitermination activities of BIV Tat $I_{79}$ mutants on the BIV TAR reporter. β-galactosidase activities determined by the ONPG assay are expressed as percent of wild-type BIV Tat peptide activity and are plotted next to activities previously determined in HeLa cells using an HIV LTR-CAT reporter. Activities determined by X-gal assays also are shown (+,-).

The capacity of the system to distinguish between different RNA-binding affinities was tested by creating a small BIV Tat peptide library in which the codon for isoleucine at position 79 was randomized. The hydrophobicity of this amino acid is important for binding to BIV TAR, and in vivo activities of 15 substitution mutants in mammalian cells are known. The library was screened on the BIV TAR reporter and plasmids were sequenced from 77 colonies displaying a variety of blue intensities. All 15 dark blue (+++) colonies encoded large hydrophobic residues (I, Y, F,and L), 29 medium blue (++) colonies generally encoded smaller hydrophobic or uncharged residues, and 31 light blue (+) or background (−) colonies generally encoded amino acids with charged or small side chains. Antitermination activities determined by β-galactosidase assays correlated qualitatively with binding activities determined in HeLa cells using HIV-LTR CAT reporter (FIG. 3). See Chen & Frankel, *Biochemistry* 33, 2708 (1994).

Example 4
Screening a Combinatorial Library of RNA binding Polypeptides

This example shows the feasibility of isolating specific RRE-binding peptides from a combinatorial library in which each position in the Rev binding domain is varied. A library was constructed with the known requirements for Rev binding in mind: TRQARRNRRRRWRR (SEQ ID NO: 1) in an a-helical context with important residues in bold; remaining residues can be replaced individually by lysines or alanines. Tan et al., *Cell* 73, 1031 (1993); Tan & Frankel, *Biochemistry* 33, 14579 (1994). A 14-mer peptide library containing any one of arginine, serine, asparagine, or histidine at each position (RSNH (SEQ ID NO: 29) library; FIG. 1B) was constructed in the context of an alanine linker, and the proportion of each amino acid was adjusted to favor arginine.

The library was encoded by a degenerate oligonucleotide having the formula: 5'-AGGAGAATCCCCATG-GCC(XYT)$_{14}$GCAGCTGCGGCGAATGCAGCAAATCCCCTG-3' (SEQ ID NO: 30), where X is a C:A mixture at a 3:1 ratio and Y is an A:G mixtures at a 1:3 ratio. Each randomized codon (XYT) encodes R:S, H:N at a ratio of 56.25% : 18.75% : 6.25%. A primer (5'-CAGGGGATTTG-CTGCATTC-3') (SEQ ID NO: 2)) was annealed to the degenerate oligonucleotide and double-stranded DNA was synthesized using Sequenase 2.0 (USB). The DNA was cloned into the BsmI and NcoI sites of pBRptacN*.

The RSNH (SEQ ID NO: 29) library was transformed into cells containing an RRE reporter vector. ~600,000 colonies (0.2% of the library) were screened, and 1920 visibly blue colonies were picked. To eliminate false positives (frequency about 0.5%), N-expressing plasmids were purified from pooled blue colonies, transformed into cells containing an RRE reporter vector and rescreened. Plasmids were then gel-purified from individual blue colonies to remove the reporter plasmid and were screened with RRE and BIV TAR reporter cells to identify N fusion proteins specific for the RRE. The majority (~85%) of N-fusion plasmids in this screen exhibited nonspecific antitermination activity, showing at least some activity on both RRE and BIV TAR reporters.

Sequences of 19 RRE-specific clones were determined and four unique sequences were found (Table 2). To eliminate false positives that may have arisen from mutations outside the cloned peptide region, oligonucleotides encodings selected positive peptides were synthesized, recloned into pBRptacN*, and plasmids were retested with RRE and BIV TAR reporter cells. All showed RRE-specific activity.

TABLE 2

Antitermination activities of the HIV Rev peptide and selected clones

|  | sequence | RRE X-gal | RRE ONPG | RRE⁻ X-gal | RRE⁻ ONPG | BIV TAR X-gal | BIV TAR ONPG |
|---|---|---|---|---|---|---|---|
| Rev | TRQARRNRRRRWRR (SEQ ID NO:1) | +++ | 66 | − | 7.5 | − | 6.6 |
| Rev (S34) | SRQARRNRRRRWRR (SEQ ID NO:3) | +++ | 50 | − | 6.8 | − | 6.9 |
| clone 24 | SRSSRRNRRRRRR (SEQ ID NO:4) | +++ | 67 | − | 8.8 | − | 8.7 |
| clone 39 | SRSRRRNRRRRRR (SEQ ID NO:5) | ++ | 54 | 13 |  | 9.5 |  |
| clone 41 | NHRRRRRHRRRRRR (SEQ ID NO:6) | + | 3.5 | − | 3.2 | − | 2.7 |
| clone 57 | NHRRRRRQRRRRRR (SEQ ID NO:7) | ++ | 12 | − | 2.5 | − | 3.1 |
| BIV Tat |  | − | 1.4 | − | 1.2 | +++ | 35 |
| mutant 41-1 | NSRRRRRHRRRRRR (SEQ ID NO:8) | − | 2.3 | − | 2.4 | − | 2.5 |
| mutant 57-1 | NSRRRRRQRRRRRR (SEQ ID NO:9) | + | 7.1 | − | 2.4 | − | 1.7 |
| mutant 57-2 | NRRRRRRQRRRRRR (SEQ ID NO:10) | − | 1.4 | − | 1.0 | − | 1.1 |
| mutant 57-3 | NHRRRRRNRRRRRR (SEQ ID NO:11) |  | 2.7 | − | 2.8 | − | 2.4 |
| mutant 57-4 | RHRRRRRQRRRRRR (SEQ ID NO:12) |  | 1.4 | − | 1.0 | − | 1.2 |

The RRE⁻ reporter contains a G46:C74 to C:G base pair substitution that markedly reduces Rev peptide binding affinity (10). Bold amino acids in Rev are important for binding, and analogous residues in the Rev-like clones 24 and 39 are indicated. Mutations in the non-Rev-like clones 41 and 57 are underlined.

Two of the four selected peptides (clones 24 and 39) were Rev-like (SRxxRRNxxxRxxx) (SEQ ID NO: 13) and exhibited specific antitermination activities comparable to the wild-type Rev peptide (Table 2). In both peptides, arginines were found at all positions in the C-terminal half of the peptide, suggesting that a high charge density may be important for binding. The two remaining peptides (clones 41 and 57) did not match the Rev consensus sequence, and clone 57 contained a glutamine residue that apparently arose from mutation of a histidine codon. The two non-Rev-like peptides exhibited weak but specific antitermination activities (Table 2). The activity of clone 41 was clearly detectable only using the colony color assay. At low activities, the colony color assay appears to be more sensitive than the ONPG assay, presumably because colony color reflects β-galactosidase activity accumulated during 48 hr of growth. The level of activity in the ONPG assay reflects activity after 1 hr of induction and depends on the rate of N-fusion protein synthesis, which may differ significantly between clones.

Because the spacing of non-arginine residues in the two non-Rev-like peptides was similar to the spacing of serine and asparagine in Rev (clones 41 and 57 have histidines at position 2 and either histidine or glutamine at position 8), the activities of several mutants were tested to assess whether the mode of binding might be related to Rev. The identities of the non-arginine side chains were found to be important for binding (Table 2) and different from the side chain requirements in Rev. In clone 57 glutamine could not be replaced by asparagine, while asparagine appears to be important at the N-terminus. Therefore, the binding modes appear to be distinct from Rev.

To confirm that the antitermination activities measured in vivo accurately reflect RNA-binding properties of the peptides, binding affinities and specificities of corresponding synthetic peptides were measured in vitro. Peptides were synthesized on an Applied Biosystems Model 432A peptide synthesizer and purified as described by Chen & Frankel, *Biochemistry* 33, 2708 (1994). All peptides were capped by a succinyl group at the N-terminus and by four alanines and an amide group at the C-terminus. Peptide concentrations were determined by tryptophan absorbance or by peptide absorbance using known peptides as standards. The purity and concentrations of peptides were confirmed by native gel electrophoresis (10% polyacrylamide in 30 mM sodium acetate, pH 4.5). Peptide molecular weights were confirmed by electrospray mass spectrometry (University of Michigan Protein and Carbohydrate Structure Facility). RNAs were transcribed in vitro using T7 RNA polymerase [Milligan & Uhlenbeck, Methods Enzymology 180, 51 (1989)] and labelled with [$\alpha$-$^{32}$p] CTP (NEN, 3000 ci/mmol). RNAs were purified and concentrations were determined as described Chen & Frankel, *Biochemistry* 33, 2708 (1994). RNA-binding gel shift assays were carried out by incubating peptide and RNA at 4° C. in 10 µl binding mixtures containing 10 mM HEPES-KOH, pH 7.5 100 mM KCl, 1 mM MgCl$_2$, 0.5 mM EDTA, 1 mM dithiothreitol, 50 µg/ml tRNA, and 10% glycerol. To determine relative binding affinities, 1–5 nM radiolabelled RNAs were titrated with peptide, and peptide-RNA complexes were resolved on 10% polyacrylamide, 0.5×TBE gels that had been prerun for 1 hr and allowed to cool to 4° C.

Figure 4A:
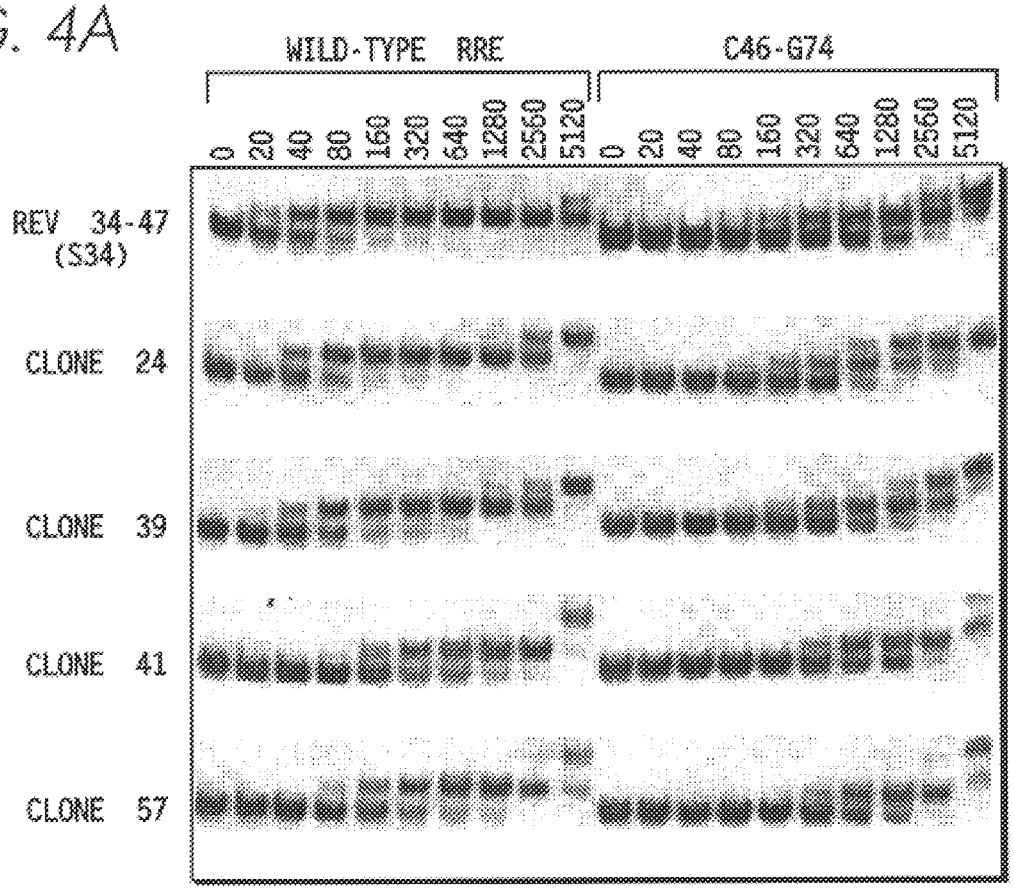
FIG. 4A: RNA-binding gel shift assay of selected peptides. Synthetic $Rev_{34-47}$ ($S_{34}$) or selected peptides were bound to wild-type or mutant RRE IIB RNA hairpins at the peptide concentrations indicated (nM).

The results from the in vitro binding assays correlated well with the antitermination assay: the two Rev-like peptides specifically bound the RRE with affinities comparable to the wild-type Rev peptide, the clone 57 peptide bound with a moderate preference for the RRE, and the clone 41 peptide bound with only a very slight preference for the RRE (FIG. 4A).

Figure 4B:
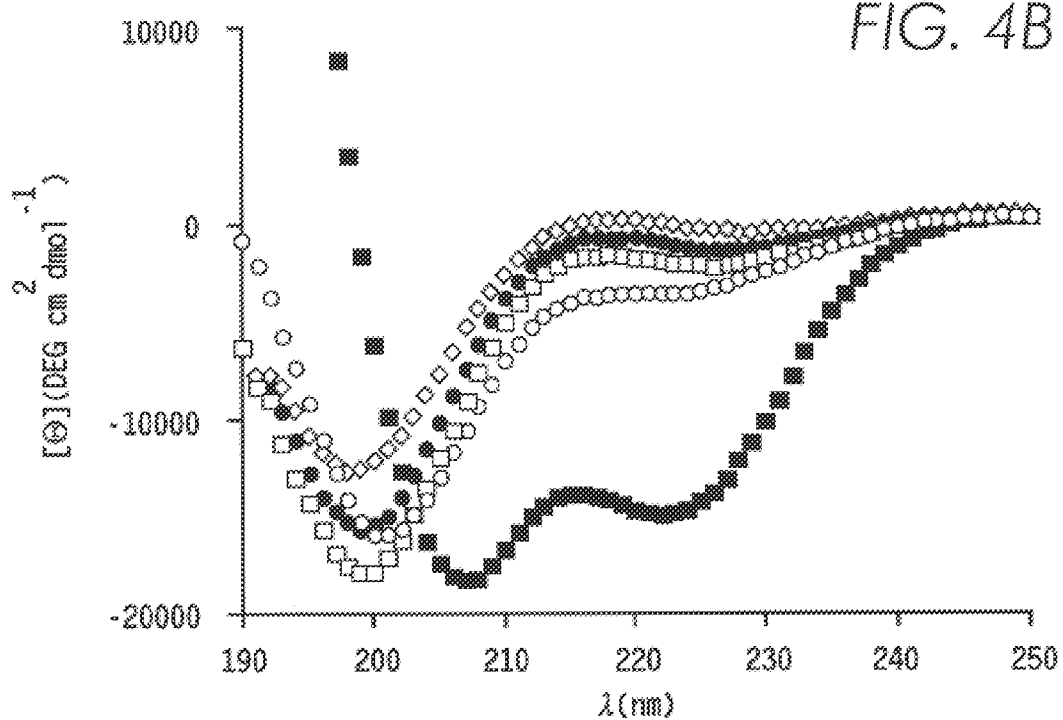
FIG. 4B: Circular dichroism spectra of $Rev_{34-40}$ (■), $Rev_{34-47}$ ($S_{34}$) (○), Rev-like peptide clone 24 (□), clone 57 peptide (●), and clone 41 peptide (◊).

Circular dichroism was used to assess whether the selected peptides adopted $\alpha$-helical conformations. Circular dichroism spectra were measured using an Aviv model 62DS spectropolarimeter. Samples were prepared in 10 mM potassium phosphate buffer, pH 7.5 and 100 mM KF. Spectra were recorded using a 1 cm pathlength cuvette at 4° C. and signal was averaged for 5 sec at each wavelength. Scans were repeated five times and averaged. Mean molecular ellipticity was calculated per amino acid residue and helical content was estimated from the value at 222 nm (Chen et al., *Biochemistry* 13, 3350 (1974). As shown in FIG. 4B, the 14 amino acid wild-type Rev peptide was somewhat less helical than the previously used 17-amino acid version (11% versus 43%), and the selected Rev-like peptides were even less helical (5–6%). The non-Rev-like peptides showed very little helix formation, probably explaining the marginal in vitro binding specificities for the RRE. The non-Rev-like peptides may be slightly more helical in the context of the N fusion proteins in vivo and therefore able to display some specific antitermination activity.

This example shows that the disclosed screening method can select RNA binding polypeptides having substantial specific binding affinity from a combinatorial library.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A method of screening a plurality of polypeptides for RNA binding activity, the method comprising:

(1) culturing a library of procaryotic cells, each cell comprising at least one vector comprising:
   a first DNA segment encoding a fusion protein comprising a fragment of a procaryotic anti-terminator protein having anti-terminator activity linked in-frame to a polypeptide under test which varies between cells in the library, and
   a second DNA segment encoding in operable linkage a promoter, an RNA recognition sequence foreign to the anti-terminator protein, a transcription termination site and a reporter gene, wherein the termination site blocks transcription of the reporter gene in the absence of a protein with anti-termination activity and affinity for the RNA recognition sequence;
   whereby the first DNA segment is expressed to yield the fusion protein, which, if the polypeptide under test has a specific affinity for the recognition sequence, binds via the polypeptide to the RNA recognition sequence of a transcript from the second DNA segment thereby inducing transcription of the second DNA segment to proceed through the termination site to the reporter gene resulting in expression of the reporter gene;

(2) detecting expression of the reporter gene in a cell from the library, the expression indicating that the cell comprises a polypeptide having RNA binding activity.

2. The method of claim 1, further comprising isolating the cell expressing the reporter gene.

3. The method of claim 2, wherein the cell line is procaryotic.

4. The method of claim 3, wherein the antiterminator protein is a phage antiterminator protein.

5. The method of claim 4, wherein the second DNA segment further encodes a Box A sequence operably linked to the RNA recognition sequence and transcription termination site.

6. The method of claim 5, wherein the cell line comprises first and second vectors, the first vector comprising the first DNA segment and the second vector comprising the second DNA segment.

7. The method of claim 1, wherein the first DNA segments comprise fragments from a cDNA or genomic library encoding the different polypeptides.

8. The method of claim 7, further comprising the step of incorporating the fragments into the vector.

9. The method of claim 1, wherein the different polypeptides vary in at least five amino acid positions.

10. The method of claim 9, wherein at least one position can be occupied by any one of at least four amino acids.

11. The method of claim 1, wherein the polypeptide contains 6–25 amino acids.

12. The method of claim 1, wherein there are at least $10^8$ different polypeptides.

13. The method of claim 1, wherein the reporter gene is a selectable gene.

14. The method of claim 13, further comprising propagating the cell line in a selectable medium to select for a cell containing a polypeptide under test with a specific affinity for the RNA recognition sequence.

15. The method of claim 14, further comprising propagating clonal colonies on a culture plate from the procaryotic cell culture.

16. The method of claim 1, wherein the rate of expression correlates with the specific affinity of the peptide for the RNA recognition sequence.

17. The method of claim 3, wherein the cell line is *E. coli*.

18. The method of claim 4, wherein the anti-terminator protein is the phage λ N protein.

19. The method of claim 18, wherein the polypeptide is a variant of the HIV Rev protein and the RNA recognition sequence is the HIV RRE sequence.

20. The method of claim 1, wherein expression is detected by FACS (Fluorescence Activated Cell Sorting).

21. A method of screening a polypeptide for RNA binding activity, the method comprising:
(1) culturing a procaryotic cell line comprising at least one vector comprising:
  a first DNA segment encoding a fusion protein comprising a procaryotic anti-terminator protein or a fragment thereof having anti-terminator activity linked in-frame to a polypeptide under test, and
  a second DNA segment encoding in operable linkage a promoter, an RNA recognition sequence foreign to the anti-terminator protein, a transcription termination site and an expression product of a reporter gene, wherein the termination site blocks transcription of the reporter gene in the absence of a polypeptide with anti-termination activity and specific affinity for the RNA recognition sequence;
  whereby the first DNA segment is expressed to yield the fusion protein, which, if the polypeptide under test has a specific affinity for the RNA recognition sequence, binds via the polypeptide to the RNA recognition sequence of a transcript from the second DNA segment thereby inducing transcription of the second DNA segment to proceed through the termination site to the reporter gene resulting in expression of the reporter gene;
(2) detecting the expression of the reporter gene to indicate that the polypeptide has specific affinity for the RNA recognition sequence.

22. A method of screening a library of RNA for binding to a selected polypeptide, the method comprising:
(1) culturing a library of procaryotic cells, each cell comprising at least one vector comprising
  a first DNA segment encoding a fusion protein comprising a fragment of a procaryotic anti-terminator protein having anti-terminator activity linked in-frame to a selected polypeptide;
  a second DNA segment encoding in operable linkage a promoter, an RNA sequence varying between different cells in the library, a termination site and a reporter gene, wherein the termination site blocks transcription of the reporter gene unless the RNA sequence has a specific affinity for the selected polypeptide;
  whereby the first DNA segment is expressed to yield the fusion protein, which, if the RNA sequence has a specific affinity for the selected polypeptide, binds via the selected polypeptide to the RNA sequence of a transcript from the second DNA segment thereby inducing transcription of the second DNA segment to proceed through the termination site to the reporter gene resulting in expression of the reporter gene;
(2) detecting expression of the reporter gene in a cell from the library, the expression indicating that the cell comprises an RNA sequence having affinity for the polypeptide.

23. A kit for screening peptides for RNA binding activity, comprising first and second DNA segments of claim 1.

* * * * *